United States Patent [19]

Salmond

[11] 4,116,985
[45] * Sep. 26, 1978

[54] NOVEL METHOD FOR PREPARING CHOLESTA-5,7-DIENE 3β,25-DIOL AND DERIVATIVES THEREOF

[75] Inventor: William G. Salmond, Kalamazoo, Mich.

[73] Assignee: The Upjohn Company, Kalamazoo, Mich.

[*] Notice: The portion of the term of this patent subsequent to Nov. 30, 1993, has been disclaimed.

[21] Appl. No.: 708,823

[22] Filed: Jul. 26, 1976

[51] Int. Cl.² .............................................. C07J 9/00
[52] U.S. Cl. .............................. 260/397.2; 260/397.4
[58] Field of Search ...................................... 260/397.2

[56] References Cited

U.S. PATENT DOCUMENTS 3,994,934  11/1976  Salmond ............................. 260/397.2
4,006,172   2/1977  Salmond ............................. 260/397.2

Primary Examiner—Elbert L. Roberts
Attorney, Agent, or Firm—Martin B. Barancik

[57] ABSTRACT

A new method for synthesizing cholesta-5,7-diene-3β,-25-diol and cholesta-5,7-diene-1α,3β,25-triol has been discovered.

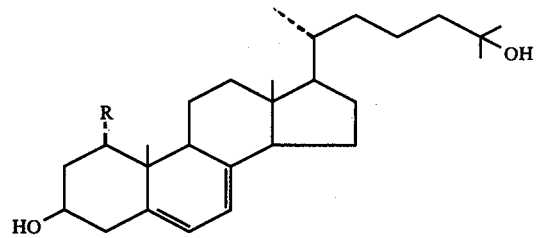

wherein R is hydrogen or hydroxy.

Various intermediates and reaction steps are claimed.

90 Claims, No Drawings

NOVEL METHOD FOR PREPARING CHOLESTA-5,7-DIENE 3β,25-DIOL AND DERIVATIVES THEREOF

BRIEF DESCRIPTION OF THE INVENTION

A new method for synthesizing cholesta-5,7-diene-3β-25-diol and cholesta-5,7-diene-1α,3β,25-triol has been discovered. These sterols are intermediates in the production of 25-hydroxy Vitamin D metabolites and their analogues, compounds useful in the treatment of various calcium metabolic disorders.

In accordance with this invention there is a process for preparing cholesta-5,7-diene-3β,-25-diol or cholesta-5,7-diene-1α, 3β,25-triol which comprises a. contacting an aldehyde of the formula

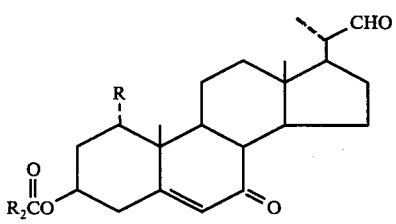

Formula II wherein R is hydrogen, hydroxy or

wherein $R_1$ and $R_2$ are the same or different and are alkyl of 1 to 6 carbon atoms, inclusive, or phenyl with an ylide of the formula

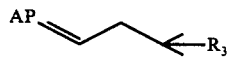

Formula III wherein A is the portion of a Wittig reagent of the type $AP=CH_2$ and is inert to the reaction medium and $R_3$ is $O^\ominus$ or

wherein $R_4$ is alkyl of one to six carbon atoms, inclusive, or phenyl to form a steroid of the formula

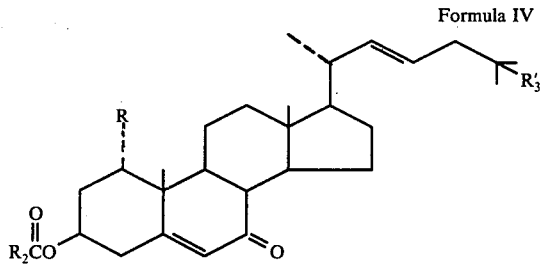

Formula IV wherein R and $R_2$ are as previously defined and $R'_3$ is $R_3$ or, upon quenching the oxyanion, OH;

b. reacting the $\Delta^{22}$ steroid formed in "a" wherein $R'_3$ is OH or

with an aryl sulfonyl hydrazide

Formula V in an organic solvent wherein $R_5$ is phenyl or phenyl substituted with one to two alkyl groups, each alkyl group being the same or different and having one to three carbon atoms, inclusive, forming a sulfonyl hydrazone of the formula Formula VI

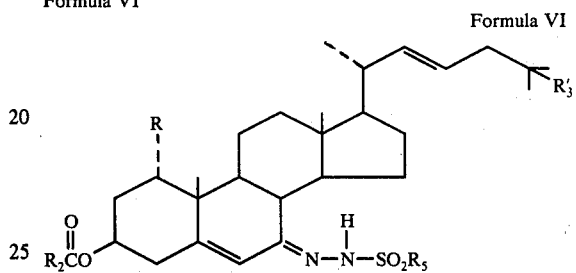

wherein R, $R_2$ and $R_5$ are as previously defined and $R'_3$ is OH or

c. contacting the sulfonyl hydrazone of "b" with a hydride in an organic solvent to form a triene of the formula

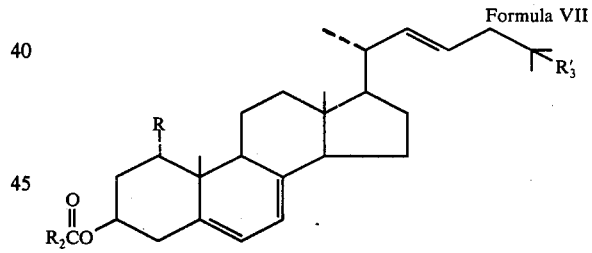

Formula VII

R, $R_2$ and $R'_3$ are as previously defined;

d. hydrolyzing the triene of "c" to form the triene of the formula

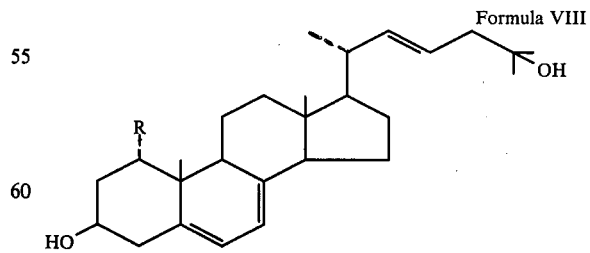

Formula VIII wherein R is hydrogen or hydroxy;

e. selectively reducing the $\Delta^{22}$ bond of the triene of step "d" with (1) biscyclopentadienyl zirconium dihydride in an organic solvent, or (2) chlorodohydridobiscyclopentadienyl zirconium in an organic solvent followed by contact with a hydride reducing agent, and f. contacting the intermediate compound formed in step "e" with acid.

A further aspect of the invention is the preparation of those sterols where R is other than hydrogen.

Another aspect of the invention is the selective reduction of the 5, 7 22 triene sterol to the 5,7 diene with the use of biscyclopentadienyl zirconium dihydride or chloridohydridobiscyclopentadienyl zirconium.

A still further aspect of the invention is the conversion of the 7-keto-22-aldehyde to the 7-keto $\Delta^{22}$ steroid wih the ylide of FIG. III.

Further aspects of the invention are novel intermediates in the synthetic route employed to obtain the cholesta-5,7-diene-3β,25-diol and cholesta-5,7-diene-1α,3β,25-triol.

DETAILED DESCRIPTION OF THE INVENTION

The phrase "alkyl of one to six carbon atoms, inclusive" covers methyl, ethyl, propyl, butyl, pentyl, hexyl and isomers thereof. Examples of isomers arre isopropyl, tert-butyl, neopentyl, and 2,3-dimethylbutyl. When a lower limitation on carbon atoms is utilized, the same type of scoping is intended.

The aldehyde of FIG. II when R is hydrogen is readily prepared by conventional methods. When R is other than hydrogen the following synthetic pathway can be utilized. A steroid of the formula

IX

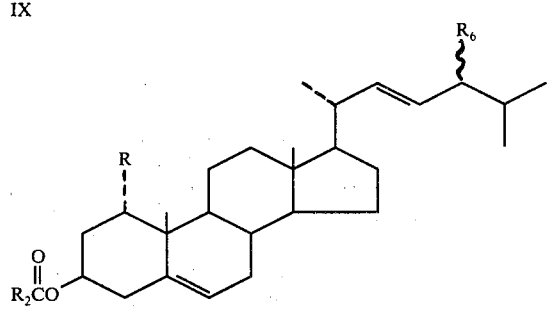

wherein R is hydroxy or

$R_1$ and $R_2$ independently selected from alkyl of one to six carbon atoms, inclusive, or phenyl, and $R_6$ is α-methyl or β-ethyl, is reacted with an allylic oxidant to form the 7-keto steroid of the formula The oxidants employed for converting a $\Delta^5$ steroid to a 7-keto-$\Delta^5$ steroid are well known in the literature, for example, see Dauben, et al. J. Org. Chem. 34, 3589 (1969); 36 3277 (1971) and U.S. Pat. No. 3,654,320. The preferred oxidant for oxidizing the $\Delta^5$ steroid of this application when R is

is a chromium trioxide-pyrazole complex. The pyrazole is of the formula

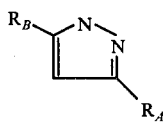

wherein $R_A$ and $R_B$ are the same or different and are hydrogen, methyl or phenyl. The preferred $R_A$ and $R_B$ substituents are methyl.

The chromium trioxide-pyrazole oxidant is prepared by adding the pyrazole to a suspension of an equal molar quantity of chromium trioxide in a solvent such as methylene chloride, chloroform or benzene. It is preferred that the solvent be methylene chloride. The mixture is stirred for 15 minutes at a temperature of −40° to 40°. It is preferred that the temperature be in the range of −25° to −15°. After the solution of the oxidant is stirred for about 15 minutes, the steroid is Formula IX added and the reaction mixture stirred until the reaction is complete as measured by TLC (thin-layer chromatography). The reaction time may be as short as one-half hour or up to about 24 hours, but usually is in the range of 2 to 6 hours. The reaction mixture is stirred preferably in a temperature range of −25° to −15°. Although the oxidation of a $\Delta^5$-steroid to the corresponding 7-keto-$\Delta^5$-steroid proceeds readily at room temperature, less chromium trioxide-pyrazole complex is required if Formula X

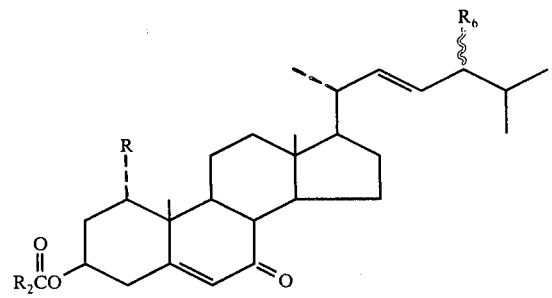

the reaction is conducted in the temperature range of −25° to −15°.

Following completion of the reaction as measured by TLC, the work-up is conducted in a manner that allows for the isolation of the pyrazole. This permits recycling of the pyrazole, an advantage in a manufacturing process. The work-up is most conveniently done by stirring the oxidation reaction mixture with a basic solution (sodium hydroxide). This causes decomposition of the chromium trioxide-pyrazole complex with the chromium salts dissolving in the aqueous phase and the pyrazole and steroid in the organic layers. The pyrazole and the steroid are then separated in a routine fashion by acid extraction of the pyrazole. The pyrazole is recovered by basification of the acidic extract using conventional techniques. The steroid is purified by means well known to those skilled in the art.

The $\Delta^{22}$ double bond of the 7-keto steroid is then selectively cleaved by ozonolysis. The ozonolysis is performed under standard conditions, for example, temperatures below about −55° C. are employed in a solvent system of a halogenated lower alkane-lower alcohol or base. The halogenated lower alkane can be chloroform, methylene chloride, dichloroethane and the like. Lower alcohols such as methanol, ethanol and isopropanol can be used. Examples of suitable bases are pyridine and lutidine.

The peroxidic products from the ozonolysis are then reduced to the aldehyde of FIG. II by standard conditions such as those set forth in Knowles et al., J. Org. Chem. 25, 1031 (1960), for example, using trimethyl phosphite as the reducing agent.

The aldehyde of Formula II wherein R is hydrogen is readily obtained. The aldehyde of Formula II where $R_1$ is hydrogen, hydroxy, or

is then reacted with an ylide of Formula III.

The ylide of Formula III is prepared by converting a betaine of the structure

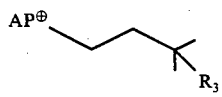

wherein $R_3$ is O⊖ or

by conventional reagents and conditions, for example, by contact with a strong base. Illustrative of the reagents which can be employed to convert the betaine to the ylide are the organo-lithium reagents, such as the alkyl lithium reagents of one to four carbon atoms, sodamide, sodium hydride, lithium amides and so forth. Art-recognized conditions are used for this reaction. The preferred reagent is n-butyl lithium.

The ylide of Formula III is then contacted with the aldehyde of Formula II to form a compound of Formula IV. The temperature at which this reaction occurs is not unduly significant. Temperature of from about 0° to about 40° C. can be employed. The preferred temperature range is from about 15° to about 25° C. It should be noted that the cation is the metal portion of the base employed to convert the betaine to the ylide.

The betaine from which the ylide is synthesized is prepared from the reaction of a methylenephosphorane

with the epoxide

The A group of the phosphorane is a group commonly employed in a Wittig reagent, see for example, Tripett; Quart. Rev. XVII, No. 4, p. 406 (1963), and House, "Modern Synthetic Reactions" second edition, p. 682–709. Additionally, the group should be substantially inert with respect to the reaction medium. Examples of such groups include triphenyl, triphenyl substituted with one to three alkyl groups on each phenyl, each alkyl group being the same or different and having from one to four carbon atoms, inclusive. Additionally, A can be a monosubstituted phenyl with two unsubstituted phenyls, for example, (phenyl)$_2$, p-carboxyphenyl. Other phosphoranes which can be used include the tris-dimethylaminomethylenephosphorane, that is (Me$_2$N)$_3$P=CH$_2$.

The phosphorane and the epoxide are reacted at room temperature or any convenient temperature of from about 0° to about 40° C., although higher or lower temperatures can be employed at times. An inert organic solvent is used as well. See Tripett and House, supra, for suitable solvents. Examples of such solvents include tetrahydrofuran, diethyl ether, hexane, pentane, benzene, heptane, octane, toluene, and dioxane.

The oxyanion betaine can be converted to the salt wherein $R_3$ is

by acylating with the desired $R_4$ acylating agent. For example, an $R_4$ acid anhydride or an $R_4$ acid halide, preferably chloride, are readily employed at standard reaction conditions.

The $\Delta^{22}$ steroid of Formula IV, prepared in the reaction of the ylide and aldehyde, is then reacted with an aryl sulfonylhydrazide, Formula V, to produce the 7-arylsulfonylhydrazone $\Delta^{22}$ steroid of Formula VI. It should be noted that during the work-up, that is "quenching" of the $\Delta^{22}$ steroid, Formula IV, formed when using the oxyanionic ylide, the anion will be changed into a hydroxy group. The aryl moiety of the sulfonyl-hydrazide can be substituted with one to two alkyl groups each being the same or different and having one to three carbon atoms, inclusive. Preferred aryl sulfonyl hydrazides are the unsubstituted phenyl and the para methyl substituted compounds.

The reaction is carried out in an organic solvent. Lower alcohols, aromatics and cyclic ethers are acceptable solvents in which to run the reaction. Examples of suitable alcohols are methanol, ethanol and isopropanol. Aryl solvents which can be used are benzene, toluene, and the xylenes. Suitable cyclic ethers are 1,4-dioxane and tetrahydrofuran.

The reaction is conveniently run at a temperature of from about 40° to about 150° C. or the refluxing temperature of the solvent system, whichever is higher. It is preferred to carry out the reaction at reflux. See also Dauben et al., J. Am. Chem. Soc., 90, 4762 (1968) and J. Org. Chem. 36, 3277 (1971).

It is preferred to carry out the reaction at reflux temperature in the presence of catalytic quantities of an acid, such as p-toluene sulfonic acid.

Since the 7-arylsulfonylhydrazone of Formula VI, preferably the phenyl or p-methylphenyl, is highly crystalline and readily isolated from reaction by-products, the 7-keto $\Delta^{22}$ steroid of Formula IV need not be specifically isolated from its by-products but can be reacted in situ with the arylsulfonylhydrazide of Formula V. The 7-arylsulfonylhydrazone group of the Formula VI compound is then removed by means of a base, such as a hydride or hydroxide, in an organic solvent to form a triene of Formula VII. Illustrative examples of hydrides or hydroxides which can remove the 7-arylsulfonylhydrazone group thereby establishing a $\Delta^7$ bond are the alkali metal hydrides such as lithium hydride, sodium hydride, and potassium hydride and the hydroxides such as potassium hydroxide. The hydrides are preferred. Organic solvents which can be employed are cyclic ethers such as 1,4-dioxane and tetrahydrofuran, substituted ethers such as 1,2-dimethoxyethane, aryl hydrocarbon solvents such as toluene, the xylenes, ethylbenzene and the like. The reaction temperature is from about 90° to about 150° C. or the reflux temperature of the solvent system, whichever is higher.

The triene of Formula VII is then isolated, followed by hydrolysis with an agent such as sodium or potassium hydroxide in an aqueous organic solvent mixture.

Suitable aqueous organic solvent mixtures are aqueous methanol, aqueous ethanol, aqueous dioxane, aqueous tetrahydrofuran, and the like. The triene di or triol of Formula VIII is the product of the hydrolysis. Alternatively, the triene of Formula VII can be hydrolyzed in situ with aqueous sodium or potassium hydroxide when 1,4-dioxane or diglyme is used as the organic solvent in the preparation of the triene of Formula VII.

The triene di- or triol of Formula VIII is then selectively reduced to form respectively the cholesta-5,7-diene-3β,25-diol and cholesta-5,7-diene-1α,3β,25-triol of Formula I. The agent which brings about the reduction of the $\Delta^{22}$ bond of the triene but leaves untouched the $\Delta^5$ and $\Delta^7$ double bonds is biscyclopentadienyl zirconium dihydride or chloridohydridobiscyclopentadienyl zirconium. The dihydride or the chlorido hydrido compound is readily prepared from biscyclopentadienylzirconiumdichloride by reduction with a hydride reducing agent such as lithium aluminum hydride or Redal ®• which hich is Na⊕ AlH$_2$(OCH$_2$CH$_2$OCH$_3$)$_2$⊖, under standard conditions, Organometallic Chemistry of Titanium, Zirconium, and Hafnium by Wailes, Coutts, and Weigold, Academic Press, N.Y., 1974, pgs. 146-150. A solution of the triene-di or triol of Formula VIII is allowed to react with a solution of the dihydride or the chlorido-hydrido compound. If the latter compound is employed an intermediate of partial structure, Formula XI is obtained.

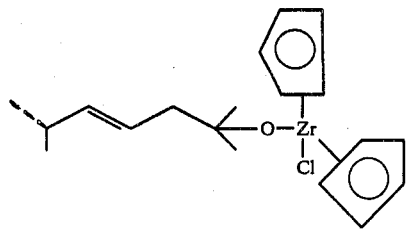

Formula XI

This intermediate structure is then further reduced with Redal ® or lithium aluminum hydride to produce a further intermediate of Formula XI wherein chlorido has been replaced by hydrido. The $\Delta^{22}$ double bond then may insert into the zirconium-hydrogen bond to form the possible cyclic oxyzirconium alkyl of partial structure Formula XII

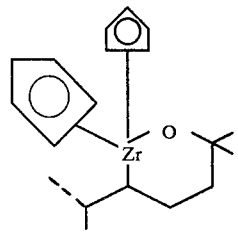

Formula XII

Where the dihydride is employed as the reducing agent, the possible intermediate of Formula XII is obtained directly.

Whatever the precise nature of the mechanism of this selective reduction and of zirconium containing intermediate(s), the final intermediate(s) is readily cleaved by contacting with acid, for example, dilute hydrochloric and sulfuric acid, ethanolic hydrogen chloride, and the like, to give the compounds of Formula I.

The conditions for selectively reducing the $\Delta^{22}$ bond of the triene are relatively simple. The reaction should be run in an organic solvent at a slightly elevated temperature range for a significant period of time. Suitable solvents are lower ethers such as tetrahydrofuran and diethylether and aryl hydrocarbon solvents such as benzene, toluene and the xylenes. Tetrahydrofuran is preferred.

The temperature at which the reaction proceeds is from about 25° C. to about 80° C., preferably 40° C. to 60° C. Depending upon the temperature and the particular rate of reaction, the reaction can proceed from 4 to 36 hours. Crystalline product is recovered from the reaction vessel. In order to remove all starting material from the product, the selective reduction is repeated.

Below are examples of the invention. These examples are not intended to limit but merely to exemplify the facets of the invention. All temperatures are in ° C. and the $R_f$'s are determined on thin layer silica gel.

EXAMPLE 1

3β,25-Dihydroxy-cholesta-5,22-diene-7-one, 3 benzoate

To a stirred suspension of methyltriphenyl phosphonium bromide (9.33 g.) in 110 ml. dry tetrahydrofuran at 0° C. is added a solution of n-butyl lithium in hexane (15%, 16.8 ml.). The mixture is then stirred at room temperature for 40 minutes and isobutylene oxide (8.5 ml.) is then added. Stirring is continued for 1.5 hours and 50 ml. dry tetrahydrofuran added. The mixture is then heated and 35 ml. liquid removed by distillation. The reaction mixture is then cooled to 0° C. and a further 16.8 ml. solution of n-butyl lithium added. The mixture is then stirred at room temperature for 40 minutes before the addition of 20S-20 formyl-3β-hydroxy-pregna-5-ene-7-one-3-benzoate (7.99 g.). After stirring for 5 minutes, the reaction is quenched with 60 ml. 1N hydrochloric acid. After conventional work-up, the product 3β-25-dihydroxy-cholesta-5,22-diene-7-one, 3-benzoate is obtained by crystallization from methanol. The product is recrystallized from cyclohexane by displacement of methylene chloride. M.P. 187°–189° C.

$R_f$(30% AcOEt/hexane): 0.4

NMR (CDCl$_3$): δ 0.71s(3H); 1.05 d(J=6)(3H); 1.17s(6H); 1.25s(3H); 4.97m(1H); 5.42m(2H); 5.75s(1H); 7.5m(3H); 8.08m(2H).

EXAMPLE 2

3β,25-Dihydroxy-cholesta-5,22-diene-7-benzenesulfonylhydrazone, 3-benzoate methanol solvate The ketone from Example 1 (5.19 g.), benzenesulfonylhydrazide (5.19 g.), p-toluenesulfonic acid (25 mg.) and methanol (100 ml.) are mixed and boiled under reflux for 4½ hours. The product crystallizes from the boiling solution. After cooling to 0° C, the product is isolated by filtration. M.P. 155°–160° C. (decomposition).

$R_f$(40% AcOEt/hexane): 0.29

NMR (CDCl$_3$): δ 0.68s(3H); 1.05d(J=6)(3H); 1.15s(3H); 1.23s(6H); 3.48s(3H); 4.92m(1H); 5.47m(2H); 6.12s(1H); 7.58m(6H); 8.0m(4H)

EXAMPLE 3

3β,25-Dihydroxy-cholesta-5,22-diene-7-benzenesulfonylhydrazone, 3-benzoate, methanol solvate In a manner analogous to Example 1, the 7-ketone is prepared but the crude product is allowed to react with benzenesulfonylhydrazide in boiling methanol. In this way the crystalline hydrazone is separated from the triphenylphosphine oxide without the isolation of the intermediate 25-hydroxy ketone.

EXAMPLE 4

3β,25-Dihydroxycholesta-5,7,22-triene, 3benzoate

A solution of 3β,25-dihydroxy-cholesta-5,22-diene-7-benzenesulfonylhydrazone, 3 benzoate, methanol solvate (1.41 g.) in 10 ml. dioxane is added dropwise during 4 hours to a boiling suspension of lithium hydride (100 mg.) in 50 ml. dioxane. The mixture is refluxed for 15 minutes after the completion of the addition, cooled and filtered. The filtrate is evaporated to give a crystalline residue and recrystallized from methanol by displacement of methylene chloride. M.P. 139°–142° C.

$R_f$(40% AcOEt/hexane): 0.52

NMR (CDCl$_3$): δ 0.67s(3H); 1.02s(3H); 1.07d(J=6)(3H); 1.20s(6H); 5.43m(4H); 7.50m(3H); 8.08m(2H)

EXAMPLE 5

Cholesta-5,7,22-triene-3β,25-diol

3β,25-Dihydroxy-cholesta-5,22-diene-7-benzenesulfonylhydrazone, 3-benzoate, methanol solvate (2.0 g.) is heated under nitrogen in dioxane (50 ml.) at 70° for 20 minutes to remove methanol. Lithium hydride (120 mg.) is then added and the mixture refluxed for one hour. The solution is cooled slightly and a solution of 0.5 g. sodium hydroxide in water (12.5 ml.) introduced. The mixture is then refluxed for one hour. After cooling, the reaction mixture separates into two phases. The lower aqueous phase is discarded. The upper organic phase is washed with saturated sodium chloride solution and again the lower aqueous phase discarded. Water (ca. 20 ml.) is then added to the dioxane solution. The product triene diol crystallizes and is isolated by filtration. M.P. 198.5°–200° C.

EXAMPLE 6

Cholesta-5,7-diene-3β,25-diol

Under a blanket of nitrogen and at room temperature a solution of Redal ® (60%) (0.8 ml.) in benzene is added to a solution of biscyclopentadienyl zirconium dichloride (650 mg.) and trienediol from Example 5 (400 mg.) in 20 ml. dry tetrahydrofuran. The mixture is then heated at 50° for 24 hours. After this period, 0.2 ml. dry acetone is added and the mixture stirred for fifteen minutes. 1.0 ml. of 6M ethanolic hydrogen chloride is added and the mixture stirred for 1 hour before pouring into cold dilute hydrochloric acid. The mixture is then extracted with chloroform. The chloroform layer is washed twice with sodium bicarbonate, dried and evaporated to leave a crystalline residue which is a mixture of the desired product and starting material trienediol in the approximate ratio of 85:15. This crystalline material is resubjected to the same reaction sequence to give pure cholesta-5,7-diene-3β,25-diol.

EXAMPLE 7

Starting with the 3-alkanoate of the aldehyde of Example 1, alkanoate being methyl, ethyl, propyl, butyl, pentyl, hexyl, or isomers thereof, the diene diol of Example 6 is prepared by the methods of Examples 1-5.

EXAMPLE 8

Starting with the 1α-hydroxy or acyloxy, acyl being alkanoyl of one to six carbon atoms, inclusive, or phenyl, substituted aldehyde of Examples 1 or 7, the dienetriol is prepared by the methods of Examples 1-5, with the proviso that in the zirconium reduction analogous to Example 6, extra zirconium reagent and Redal ® are required because of the presence of the additional hydroxyl groups. Thus, on the same molar scale as Example 6, 416 mg. triene triol, 1.2 ml. Redal ® solution and 1.0 g. biscyclopentadienyl zirconium dichloride are used.

I claim:

1. A process for preparing cholesta-5,7-diene-3β,25-diol or cholesta-5,7-diene-1α,3β,25-triol which comprises a. contacting an aldehyde of the formula

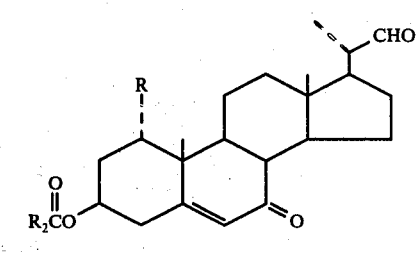

wherein R is hydrogen, hydroxy or

wherein $R_1$ and $R_2$ are the same or different and are alkyl of one to six carbon atoms, inclusive, or phenyl
with an ylide of the formula

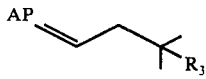

wherein A is the portion of a Wittig reagent of the type $AP=CH_2$ and is inert to the reaction medium and $R_3$ is $O\ominus$ or

wherein $R_4$ is alkyl of one to six carbon atoms, inclusive, or phenyl to form a steroid of the formula

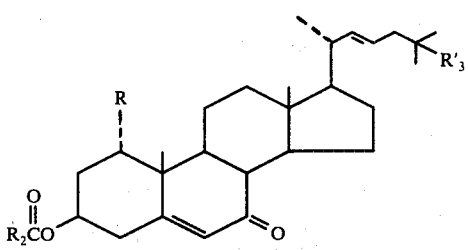

wherein R and $R_2$ are as defined previously and $R'_3$ is $R_3$ or, upon quenching the oxyanion, OH, b. reacting the $\Delta^{22}$ steroid formed in "a" wherein $R'_3$ is OH or

with an aryl sulfonyl hydrazide

in an organic solvent wherein $R_5$ is phenyl or phenyl substituted with one to two alkyl groups, each alkyl group being the same or different and having one to three carbon atoms, inclusive, forming a sulfonyl hydrazone of the formula

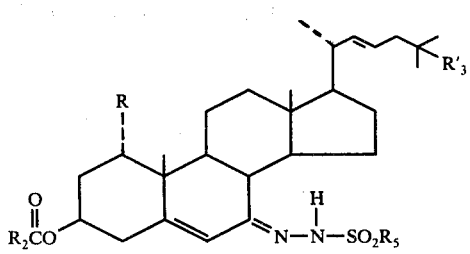

wherein R, $R_2$ and $R_5$ are as previously defined and $R'_3$ is OH or

c. contacting the sulfonyl hydrazone of "b" with a hydride in an organic solvent to form a triene of the formula

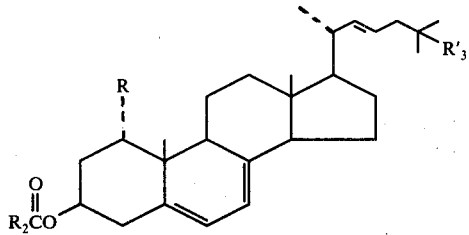

R, $R_2$ and $R'_3$ are as previously defined;

d. hydrolyzing the triene of "c" to form the triene of the formula

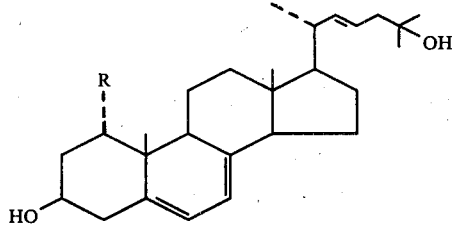

wherein R is hydrogen or hydroxy;

e. selectively reducing the $\Delta^{22}$ bond of the triene of step "d" with
  (1) biscyclopentadienyl zirconium dihydride in an organic solvent, or
  (2) chloridohydridobiscyclopentadienyl zirconium in an organic solvent followed by contact with a hydride reducing agent, and f. contacting the compound formed in step "e" with acid.

2. A process in accordance with claim 1 wherein R is hydrogen.

3. A process in accordance with claim 1 wherein R is hydroxy or

4. A process in accordance with claim 2 wherein $R_2$ is phenyl.

5. A process in accordance with claim 3 wherein $R_2$ is phenyl.

6. A process in accordance with claim 2 wherein $R'_3$ is hydroxy.

7. A process in accordance with claim 3 wherein $R'_3$ is hydroxy.

8. A process in accordance with claim 6 wherein $R_5$ is phenyl or p-methylphenyl.

9. A process in accordance with claim 1 for preparing an aldehyde of the formula

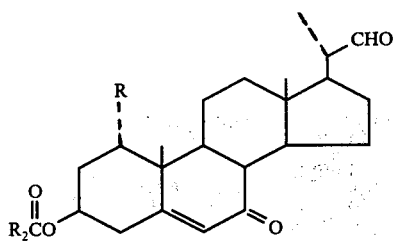

wherein R is hydroxy or

wherein $R_1$ and $R_2$ are independently alkyl of one to six carbon atoms, inclusive, or phenyl, which comprises
  a. oxidizing Formula IV

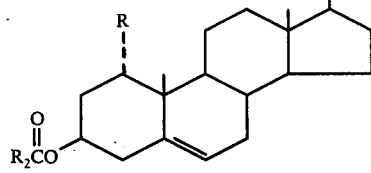

wherein R is hydroxy or

$R_1$ and $R_2$ independently selected from alkyl of one to six carbon atoms, inclusive, or phenyl, and $R_6$ is α-methyl or β-ethyl to form the 7-keto steroid

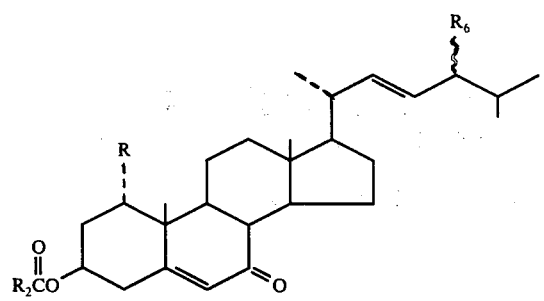

b. ozonizing the 7-keto steroid formed in step "a" to form peroxidic products;
  c. reducing the peroxidic products formed in step "b" to make the aldehyde of the preamble of this claim.

10. A process in accordance with claim 9 wherein R is hydroxy.

11. A process in accordance with claim 9 wherein R is

12. A process in accordance with claim 10 wherein $R_2$ is phenyl.

13. A process in accordance with claim 11 wherein $R_2$ is phenyl.

14. A process in accordance with claim 9 wherein $R_6$ is α-methyl.

15. A process in accordance with claim 9 wherein $R_6$ is β-ethyl.

16. A process in accordance with claim 10 wherein $R_6$ is α-methyl.

17. A process in accordance with claim 11 wherein $R_6$ is β-ethyl.

18. A compound of the formula

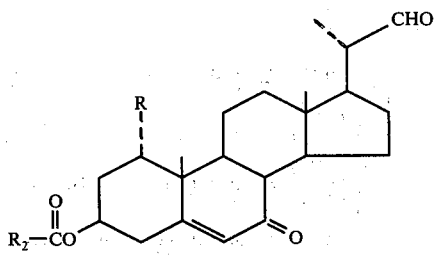

wherein R is hydrogen, hydroxy or

wherein $R_1$ and $R_2$ are alkyl of one to six carbon atoms, inclusive, or phenyl, with the proviso that when R is hydrogen, $R_2$ is phenyl.

19. The compound in accordance with claim 18 wherein R is hydrogen.

20. A compound in accordance with claim 18 wherein R is hydroxy.

21. A compound in accordance with claim 18 wherein R is

22. A compound of the formula

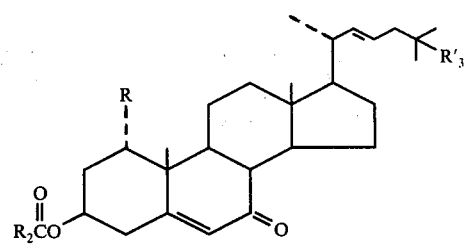

wherein R is hydrogen, hydroxy or

$R_1$ and $R_2$ are the same or different and are alkyl of one to six carbon atoms, inclusive, or phenyl, $R'_3$ is $O\ominus$, hydroxy, or

wherein R$_4$ is alkyl of one to six carbon atoms, inclusive, or phenyl.

23. A compound in accordance with claim 22 wherein R is hydrogen.

24. A compound in accordance with claim 22 wherein R is hydroxy.

25. A compound in accordance with claim 22 wherein R is

26. A compound in accordance with claim 23 wherein R$_2$ is phenyl.

27. A compound in accordance with claim 24 wherein R$_2$ is phenyl.

28. A compound in accordance with claim 25 wherein R$_2$ is phenyl.

29. A compound in accordance with claim 22 wherein R'$_3$ is hydroxy.

30. A compound in accordance with claim 23 wherein R'$_3$ is hydroxy.

31. A compound in accordance with claim 24 wherein R'$_3$ is hydroxy.

32. A compound in accordance with claim 26 wherein R'$_3$ is hydroxy.

33. A compound of the formula

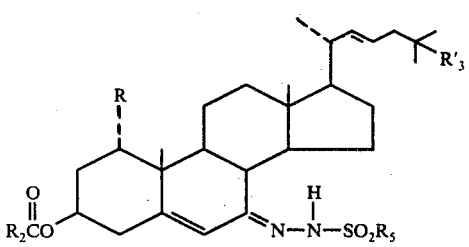

wherein R is hydrogen, hydroxy or

wherein R$_1$ is alkyl of one to six carbon atoms, inclusive, or phenyl; R$_2$ is alkyl of one to six carbon atoms, inclusive, or phenyl; R'$_3$ is O$\ominus$, hydroxy, or

wherein R$_4$ is alkyl of one to six carbon atoms, inclusive, or phenyl; and R$_5$ is phenyl or phenyl substituted with one to two alkyl groups, each alkyl being the same or different and having one to three carbon atoms, inclusive.

34. A compound in accordance with claim 33 wherein R is hydrogen.

35. A compound in accordance with claim 33 wherein R is hydroxy or

36. A compound in accordance with claim 33 wherein R$_2$ is phenyl.

37. A compound in accordance with claim 33 wherein R'$_3$ is hydroxy.

38. A compound in accordance with claim 33 wherein R$_5$ is phenyl or p-methylphenyl.

39. A compound in accordance with claim 34 wherein R'$_3$ is hydroxy and R$_5$ is phenyl or p-methylphenyl.

40. A compound in accordance with claim 35 wherein R'$_3$ is hydroxy and R$_5$ is phenyl or p-methylphenyl.

41. A compound in accordance with claim 39 wherein R$_2$ is phenyl.

42. A compound in accordance with claim 40 wherein R$_2$ is phenyl.

43. A process for preparing a compound of the formula

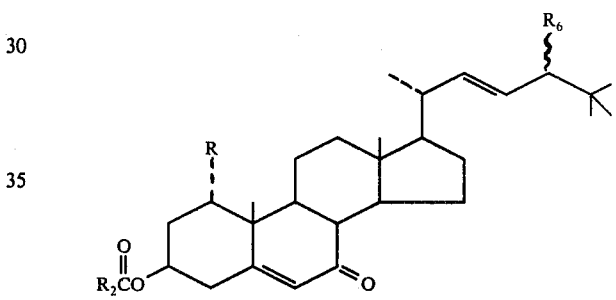

wherein R is

R$_1$ and R$_2$ are independently alkyl of one to six carbon atoms, inclusive, or phenyl; and R$_6$ is α-methyl or β-ethyl which comprises oxidizing

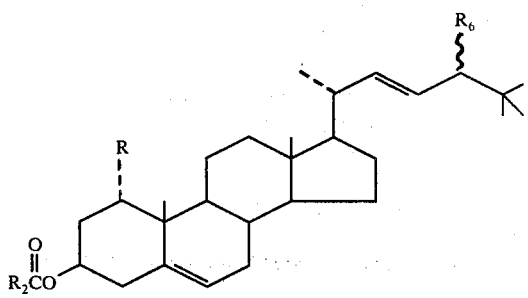

wherein R, R$_2$ and R$_6$ are as defined above, with a chromium trioxidepyrazole complex, the pyrazole of the formula

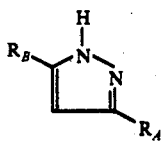

wherein $R_A$ and $R_B$ are the same or different and are hydrogen, methyl, or phenyl.

44. A process in accordance with claim 43 wherein $R_1$ is methyl.

45. A process in accordance with claim 43 wherein $R_6$ is β-ethyl.

46. A process in accordance with claim 44 wherein $R_2$ is phenyl.

47. A process in accordance with claim 45 wherein $R_2$ is phenyl.

48. A process in accordance with claim 43 wherein $R_A$ and $R_B$ are methyl.

49. A process for preparing a compound of the formula

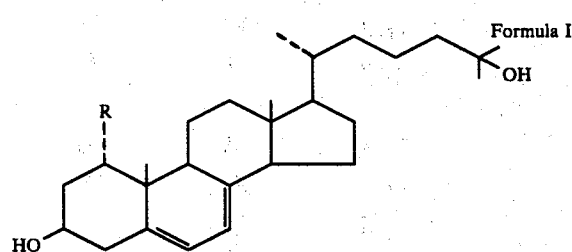

Formula I wherein R is hydrogen or hydroxy which comprises
a. selectively reducing a compound of the formula

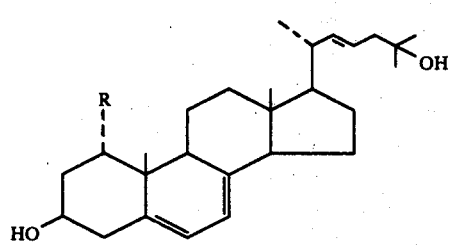

wherein R is hydrogen or hydroxy with
(1) biscyclopentadienyl zirconium dihydride in an organic solvent or
(2) chloridohydridobiscyclopentadienyl zirconium in an organic solvent followed by contact with a hydride reducing agent and
b. contacting the compound formed in step a with acid.

50. A process in accordance with claim 49 wherein biscyclopentadienyl zirconium dihydride is used.

51. A process in accordance with claim 50 wherein R is hydrogen.

52. A process in accordance with claim 49 wherein chloridohydridobiscyclopentadienyl zirconium is used.

53. A process in accordance with claim 50 wherein R is hydroxy.

54. A process in accordance with claim 52 wherein R is hydrogen.

55. A process in accordance with claim 52 wherein R is hydroxy.

56. A process in accordance with claim 52 wherein the hydride reducing agent is $Na^+AlH_2(OCH_2CH_2OCH_3)_2^-$.

57. A compound in accordance with claim 20 wherein $R_2$ is methyl.

58. A compound in accordance with claim 21 wherein $R_1$ and $R_2$ are methyl.

59. A compound in accordance with claim 21 wherein $R_1$ and $R_2$ are phenyl.

60. A compound in accordance with claim 21 wherein $R_1$ is methyl and $R_2$ is phenyl.

61. A compound in accordance with claim 21 wherein $R_1$ is phenyl and $R_2$ is methyl.

62. A compound in accordance with claim 28 wherein $R_1$ is methyl and $R'_3$ is hydroxy.

63. A compound in accordance with claim 28 wherein $R_1$ is methyl and $R'_3$ is

wherein $R_4$ is methyl.

64. A compound in accordance with claim 25 wherein $R_1$ is methyl, $R_2$ is methyl, and $R_3'$ is

wherein $R_4$ is methyl.

65. A process in accordance with claim 52 wherein the hydride reducing agent is lithium aluminum hydride.

66. A process in accordance with claim 1 wherein $R_3$ is $O\ominus$.

67. A process in accordance with claim 9 wherein $R_3$ is $O\ominus$.

68. A process in accordance with claim 1 wherein $R'_3$ is hydroxy.

69. A process in accordance with claim 9 wherein $R'_3$ is hydroxy.

70. A process in accordance with claim 2 wherein $R_3$ is $O\ominus$.

71. A process in accordance with claim 3 wherein $R_3$ is $O\ominus$.

72. A compound in accordance with claim 22 wherein $R'_3$ is hydroxy.

73. A compound in accordance with claim 23 wherein $R'_3$ is hydroxy.

74. A compound in accordance with claim 24 wherein $R'_3$ is hydroxy.

75. A compound in accordance with claim 25 wherein $R'_3$ is hydroxy.

76. A process for preparing an aldehyde of the formula

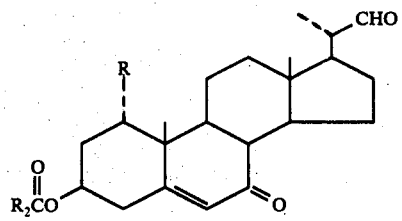

wherein R is hydroxy or

wherein $R_1$ and $R_2$ are independently alkyl of one to six carbon atoms, inclusive, or phenyl, which comprises a. oxidizing

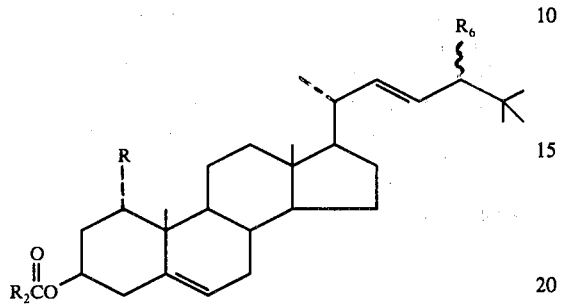

wherein R is hydroxy or

$R_1$ and $R_2$ are independently alkyl of one to six carbon atoms, inclusive, or phenyl, and $R_6$ is α-methyl or β-ethyl to form the 7keto steroid

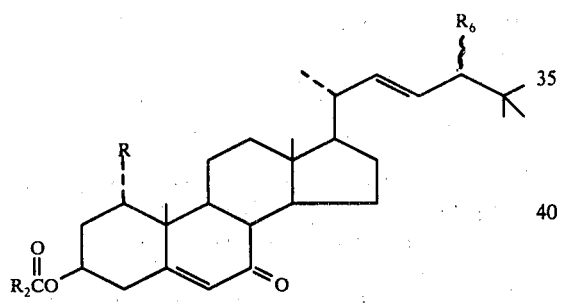

b. ozonolyzing the $\Delta^{22}$ bond of the 7-keto steroid formed in step "a" to form the peroxidic products;

c. reducing the peroxidic products formed in step "b" to make the aldehyde of the preamble.

77. A process in accordance with claim 76 wherein R is hydroxy.

78. A process in accordance with claim 76 wherein R is

79. A process in accordance with claim 77 wherein $R_2$ is phenyl.

80. A process in accordance with claim 78 wherein $R_2$ is phenyl.

81. A process in accordance with claim 76 wherein $R_6$ is α-methyl.

82. A process in accordance with claim 76 wherein $R_6$ is β-ethyl.

83. A method for preparing a compound of the formula

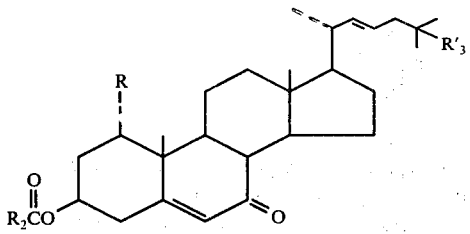

wherein R is hydrogen, hydroxy or

wherein $R_1$ and $R_2$ are independently alkyl of one to six carbon atoms, inclusive, or phenyl, and $R_3$ is $O\ominus$ or

wherein $R_4$ is alkyl of one to six carbon atoms, inclusive, or phenyl, which comprises reacting an aldehyde of the formula

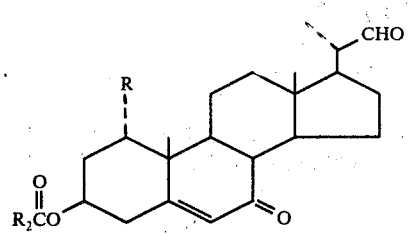

wherein R is hydrogen, hydroxy or

wherein $R_1$ and $R_2$ are alkyl of one to six carbon atoms, inclusive, or phenyl, with an ylide of the formula

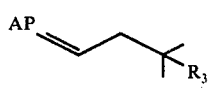

wherein A is the portion of a Wittig reagent of the type $AP=CH_2$ and is inert to the reaction medium and $R_3$ is $O\ominus$ or

wherein $R_4$ is alkyl of one to six carbon atoms, inclusive, or phenyl.

84. A process in accordance with claim 83 wherein R is hydrogen.

85. A process in accordance with claim 83 wherein R is hydroxy or

86. A process in accordance with claim 83 wherein $R_2$ is phenyl.
87. A process in accordance with claim 83 wherein $R_3$ is $O^\ominus$.
88. A process in accordance with claim 87 wherein R is hydrogen.
89. A process in accordance with claim 87 wherein R is hydroxy or
90. A process in accordance with claim 87 wherein $R_2$ is phenyl.
* * * * *